US006277451B1

(12) United States Patent
Mehl et al.

(10) Patent No.: US 6,277,451 B1
(45) Date of Patent: *Aug. 21, 2001

(54) LIQUID CRYSTAL MATERIALS AND DEVICES

(75) Inventors: Georg H Mehl; John W Goodby, both of Hull (GB)

(73) Assignee: The Secretary of State for Defence in Her Britannic Majesty's Government of the United Kingdom of Great Britain and Northern Ireland, Farnborough (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/125,592

(22) PCT Filed: Mar. 27, 1997

(86) PCT No.: PCT/GB97/00860

§ 371 Date: Aug. 21, 1998

§ 102(e) Date: Aug. 21, 1998

(87) PCT Pub. No.: WO97/36908

PCT Pub. Date: Oct. 9, 1997

(30) Foreign Application Priority Data

Mar. 29, 1996 (GB) .................................................. 960678

(51) Int. Cl.[7] .......................... C09K 19/34; C09K 19/30; G02F 1/133; C07F 7/21; C07F 7/08; C08G 77/04

(52) U.S. Cl. ................ 428/1.1; 252/299.61; 252/299.63; 349/2; 556/482; 528/33

(58) Field of Search ............... 252/299.01, 299.61, 252/299.63, 62.9; 349/2; 428/1.1; 528/33; 556/482

(56) References Cited

U.S. PATENT DOCUMENTS

| 5,442,025 | * | 8/1995 | Spes et al. | 528/15 |
| 5,484,867 | * | 1/1996 | Lichtenhan et al. | 528/9 |
| 5,773,179 | * | 6/1998 | Mehl et al. | 430/20 |
| 6,184,322 | * | 2/2001 | Styring et al. | 252/299.61 |

FOREIGN PATENT DOCUMENTS

| 0 163 495 | 12/1985 | (EP) . |
| 0 446 912 | 9/1991 | (EP) . |
| 6 118 396 | 4/1994 | (JP) . |

OTHER PUBLICATIONS

Polym. Prepr. (AM. Chem. Soc., Div. Polym. Chem.) (Acppay,00323934); 1994 vol. 35 (2); pp. 665–666, University Michigan;Department Materials Science Engineering; Ann Arbor; 48109–2136; MI; USA (US), XP000675493 Sellinger A et al: Coupling of allyloxy and propargyloxy moieties with hydridosilanes: novel liquid crystalline functionalized silsesquioxanes: see the whole document.

Macromolecular Chemistry and Physics, vol. 197, No. 2, Feb. 1, 1996, pp. 745–752, XP000588418 XIE P et al: "Synthesis and Mesomorphic Properties of Fishbone–Like Liquid Crystalline Polysilsesquioxanes, 3 Fishbone–Like, Axo–Based Liquid Crystalline Polysilsesquioxane" see the whole document.

Angew. Chem., Int. Ed. Engl. (Acieay,05700833);1996, vol. 35 (22); pp. 2641–2643, Univ. of Hull; School of Chemistry; Hull; 67RX; UK (GB), XP000674567 Mehl G H et al: "liquid–crystalline, substituted octakis(dimethisiloxy)octasilsesqui oxanes: oligomeric supermolecular materials with defined topology" see the whole document.

Chem. Ber. (ChBeam,00092940); 1996, vol. 129(5); pp. 521–525, Univ. Hull;School Chemisstry; Hull; HU6 7RX; UK (GB), XP000675492 Mehl G H et al: "Supermolecules containing a tetrahedral core: a new class of liquid–crystalline siloxanes" see the whole document.

* cited by examiner

Primary Examiner—Shean C. Wu
(74) Attorney, Agent, or Firm—Nixon & Vanderhye

(57) ABSTRACT

Materials of formula (I): $[G]_g(SiO_{1/2})_x$ are described where G is $R_3SiR_1R_2(O)_k$; $R_1$, $R_2$, $R_3$ are independently a $C_{1-16}$ alkyl which may be partly or fully halogenated, H and formula (IA), wherein Y is selected from COO, OCO, O, S, CHOH, CHF, $CH_2$; $Q=(CH_2)_n$ where one or more non-adjacent methylenes may be replaced by O and n=1=20; Z is O, S, a single covalent bond, COO, OCO; when Y is $CH_2$, then n may also be 0;

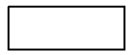

(a) represents any mesogenic group; provided that at least one of $R_1$, $R_2$, $R_3$, is selected from formula (IA):

IA k=0 or 1; g=4 or 6 or 8 or 10 or 12; 1=3 or 8 provided that: if k=1, 1=3 and x is selected form 6, 8, 10, 12 then g=x; if k=0, 1=8 and g=4 then x=1; and further provided that G may have up to g different structures for any single compound. Pyroelectric and piezoelectric devices, liquid crystal electro-optical display devices and optical recording media containing the adsorbed liquid crystals mixed with other liquid crystal materials are described.

17 Claims, 3 Drawing Sheets

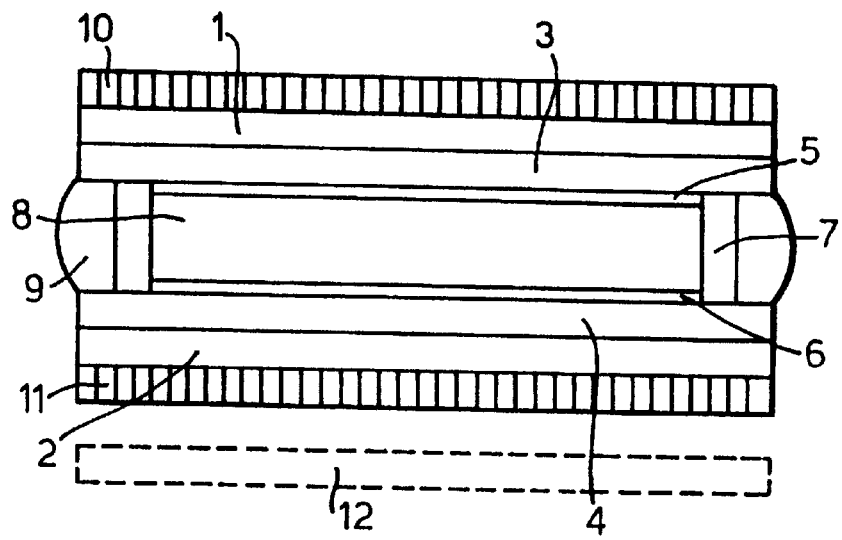
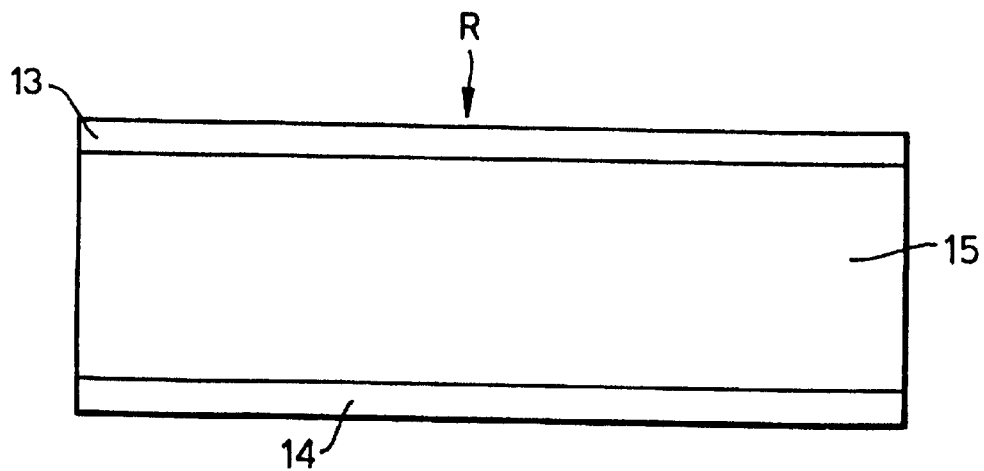

LIQUID CRYSTAL MATERIALS AND DEVICES

This application is a 35 U.S.C. 371 of PCT/GB97/00860 filed Mar. 27, 1999.

This invention concerns liquid crystal materials, and their use in liquid crystal mixtures and devices.

BACKGROUND OF THE INVENTION

Liquid crystals can exist in various phases. In essence there are three different classes of liquid crystalline material, each possessing a characteristic molecular arrangement. These classes are nematic, chiral nematic (cholesteric) and smectic. A wide range of smectic phases exists, for example smectic A and smectic C. Some liquid crystal materials possess a number of liquid crystal phases on varying the temperature, others have just one phase. For example, a liquid crystal material may show the following phases on being cooled from the isotropic phase:—isotropic—nematic—smectic A—smectic C—solid. If a material is described as being smectic A then it means that the material possesses a smectic A phase over a useful working temperature range.

Materials possessing a smectic A ($S_A$) phase may exhibit an electroclinic effect. The electroclinic effect was first described by S Garoff and R Meyer, Phys. Rev. Lett., 38, 848 (1977). An electroclinic device has also been described in UK patent application GB-2 244 566 A. This particular device helps to overcome the poor alignment problems of electroclinic (EC) devices using a surface alignment that gives a surface tilt within a small range of angles.

When a smectic A phase is composed of chiral molecules, it may exhibit an electroclinic effect, i.e. a direct coupling of molecular tilt to applied field. The origin of the electroclinic effect in a smectic A phase composed of chiral polar molecules has been described by Garoff and Meyer as follows. The application of an electric field parallel to the smectic layers of such a smectic A phase biases the free rotation of the transverse molecular dipoles and therefore produces a non-zero average of the transverse component of the molecular polarisation. When such a dipole moment is present and coupled to the molecular chirality, a tilt of the long molecular axis (the director) is induced in a plane perpendicular to the dipole moment.

In thin samples, for example 1–3 μm, and with the smectic layers tilted or perpendicular with respect to the glass plates the electroclinic effect is detectable at low applied fields.

In an aligned smectic A sample a tilt of the director is directly related to a tilt of the optic axis. The electroclinic effect results in a linear electro-optic response. The electro-optic effect can manifest itself as a modulation of the effective birefringence of the device.

Electroclinic (EC) devices are useful, for example, in spatial light modulators having an output that varies linearly with applied voltage. A further advantage of EC devices is that they have high speed response times, much faster than twisted nematic type devices. One known type of ferroelectric device is bistable, in contrast the EC device is not bistable and has an output that varies linearly with applied voltage.

The electroclinic effect is sometimes referred to as the soft-mode effect see G Andersson et al in Appl. Phys. Lett., 51, 9, (1987).

In general terms, regarding the electroclinic effect, it is advantageous if on applying a small voltage there results a large induced tilt. An increase in induced tilt may result in an increase in contrast ratio. It is also advantageous if a large induced tilt can be obtained at as low a voltage as possible.

It is also advantageous if the relationship between molecular induced tilt and applied voltage is temperature independent. When an increase in applied voltage results in little or no change in induced tilt then the material being tested is generally referred to as exhibiting a saturation voltage effect. By $S_A^*$ is meant a $S_A$ phase which contains some proportion of chiral molecules. Cholesteric or chiral nematic liquid crystals possess a twisted helical structure which is capable of responding to a temperature change through a change in the helical pitch length. Therefore as the temperature is changed, then the wavelength of the light reflected from the planar cholesteric structure will change and if the reflected light covers the visible range then distinct changes in colour occur as the temperature varies. This means that there are many possible applications including the areas of thermography and thermooptics.

The cholesteric mesophase differs from the nematic phase in that in the cholesteric phase the director is not constant in space but undergoes a helical distortion. The pitch length for the helix is a measure of the distance for the director to turn through 360°.

By definition, a cholesteric material is chiral material. Cholesteric materials may also be used in electro-optical displays as dopants, for example in twisted nematic displays where they may be used to remove reverse twist defects. They may also be used in cholesteric to nematic dyed phase change displays where they may be used to enhance contrast by preventing wave-guiding.

Thermochromic applications of cholesteric liquid crystal materials usually use thin film preparations of the materials which are then viewed against a black background. These temperature sensing devices may be placed into a number of applications involving thermometry, medical thermography, non-destructive testing, radiation sensing and for decorative purposes. Examples of these may be found in D G McDonnell in Thermotropic Liquid Crystals, Critical Reports on Applied Chemistry, Vol. 22, edited by G W Gray, 1987 pp 120–44; this reference also contains a general description of thermochromic cholesteric liquid crystals.

Generally, commercial thermochromic applications require the formulation of mixtures which possess low melting points, short pitch lengths and smectic transitions just below the required temperature-sensing region. Preferably the mixture or material should retain a low melting point and high smectic—cholesteric transition temperatures.

In general, thermochromic liquid crystal devices have a thin film of cholesterogen sandwiched between a transparent supporting substrate and a black absorbing layer. One of the fabrication methods involves producing an 'ink' with the liquid crystal by encapsulating it in a polymer and using printing technologies to apply it to the supporting substrate. Methods of manufacturing the inks include gelatin microencapsulation, U.S. Pat. No. 3,585,318 and polymer dispersion, U.S. Pat. Nos. 1,161,039 and 3,872,050. One of the ways for preparing well-aligned thin-film structures of cholesteric liquid crystals involves laminating the liquid crystal between two embossed plastic sheets. This technique is described in UK patent 2,143,323.

Ferroelectric smectic liquid crystal materials, which can be produced by mixing an achiral host and a chiral dopant, use the ferroelectric properties of the tilted chiral smectic C, F, G, H, I, J and K phases. The chiral smectic C phase is denoted $S_C^*$ with the asterisk denoting chirality. The $S_C$ phase is generally considered to be the most useful as it is the least viscous. Ferroelectric smectic liquid crystal materials should ideally possess the following characteristics: low viscosity, controllable spontaneous polarisation (Ps) and an $S_C$ phase that persists over a broad temperature range which should include ambient temperature and exhibits chemical and photochemical stability. Materials which possess these characteristics offer the prospect of very fast switching liquid crystal containing devices. Some applications of ferroelectric liquid crystals are described by J S Patel and J W Goodby in Opt. Eng., 1987, 26, 273.

In ferroelectric liquid crystal devices the molecules switch between different alignment directions depending on the polarity of an applied electric field. These devices can be arranged to exhibit bistability where the molecules tend to remain in one of two states until switched to the other switched state. Such devices are termed surface stabilised ferroelectric devices, e.g. as described in U.S. Pat. No. 5,061,047 and U.S. Pat. No. 4,367,924 and U.S. Pat. No. 4,563,059. This bistability allows the multiplex addressing of quite large and complex devices.

One common multiplex display has display elements, i.e. pixels, arranged in an X, Y matrix format for the display of for example alpha numeric characters. The matrix format is provided by forming the electrodes on one slide as a series of column electrodes, and the electrodes on the other slide as a series of row electrodes. The intersections between each column and row form addressable elements or pixels. Other matrix layouts are known, e.g. seven bar numeric displays.

There are many different multiplex addressing schemes. A common feature involves the application of a voltage, called a strobe voltage to each row or line in sequence. Coincidentally with the strobe applied at each row, appropriate voltages, called data voltages, are applied to all column electrodes. The differences between the different schemes lies in the shape of the strobe and data voltage waveforms.

Other addressing schemes are described in GB-2,146, 473-A; GB-2,173,336-A; GB-2,173,337-A; GB-2,173629-A; WO 89/05025; Harada et al 1985 S.I.D. Paper 8.4 pp 131–134; Lagerwall et al 1985 I.D.R.C. pp 213–221 and P Maltese et al in Proc 1988 I.D.R.C. pp 90–101 Fast Addressing for Ferroelectric LC Display Panels.

The material may be switched between its two states by two strobe pulses of opposite sign, in conjunction with a data waveform. Alternatively, a blanking pulse may be used to switch the material into one of its states. Periodically the sign of the blanking and the strobe pulses may be alternated to maintain a net d.c. value.

These blanking pulses are normally greater in amplitude and length of application than the strobe pulses so that the material switches irrespective of which of the two data waveforms is applied to any one intersection. Blanking pulses may be applied on a line by line basis ahead of the strobe, or the whole display may be blanked at one time, or a group of lines may be simultaneously blanked.

It is well known in the field of ferroelectric liquid crystal device technology that in order to achieve the highest performance from devices, it is important to use mixtures of compounds which give materials possessing the most suitable ferroelectric smectic characteristics for particular types of devices.

Devices can be assessed for speed by consideration of the response time vs pulse voltage curve. This relationship may show a minimum in the switching time ($t_{min}$) at a particular applied voltage ($V_{min}$). At voltages higher or lower than $V_{min}$ the switching time is longer than $t_{min}$. It is well understood that devices having such a minimum in their response time vs voltage curve can be multiplex driven at high duty ratio with higher contrast than other ferroelectric liquid crystal devices. It is preferred that the said minimum in the response time vs voltage curve should occur at low applied voltage and at short pulse length respectively to allow the device to be driven using a low voltage source and fast frame address refresh rate.

Typical known materials (where materials are a mixture of compounds having suitable liquid crystal characteristics) which do not allow such a minimum when included in a ferroelectric device include the commercially available materials known as SCE13 and ZLI-3654 (both supplied by Merck UK Ltd, Poole, Dorset). A device which does show such a minimum may be constructed according to PCT GB 88/01004 and utilising materials such as e.g. commercially available SCE8 (Merck UK Ltd). Other examples of prior art materials are exemplified by PCT/GB 86/00040, PCT GB 87100441 and UK 2232416B.

The unit that is the basic building block of a polymer is called a monomer.

The polymerisation process i.e. the formation of a polymer from its constituent monomers does not usually create polymers of uniform molecular weight, rather what is created is a distribution of molecular weights. In order to describe a sample of polymer it is necessary to state the average number of monomers in a polymer this is called the degree of polymerisation (D.P). By how much the majority of polymer molecules differ from this average value (or to describe the spread of molecular weight) is called the polydispersity.

A number of different average molecular weights can be drawn from gel permeation chromatography (GPC) for a given sample including: $M_n$—number average molecular weight and $M_w$—weight average molecular weight. The value used to calculate D.P. is usually $M_n$ and polydispersity is usually defined as $M_w/M_n$.

Polymers can be made from different types of monomers, in which case the polymer is called a co-polymer. If two types of monomer join in a random fashion then the polymer is called a random co-polymer. If the two monomers form short sequences of one type first which then combine to form the final polymer then a block copolymer results. If short sequences of one of the monomers attach themselves as side chains to long sequences consisting of the other type of monomer then the polymer is referred to as a graft copolymer.

In liquid crystal (LC) polymers the monomers can be attached together in essentially two ways. The liquid crystal part or mesogenic unit of the polymer may be part of the polymer backbone resulting in a main chain LC polymer. Alternatively, the mesogenic unit may be attached to the polymer backbone as a pendant group i.e. extending away from the polymer backbone; this results in a side-chain LC polymer. These different types of polymer liquid crystal are represented schematically below. The mesogenic units are depicted by the rectangles.

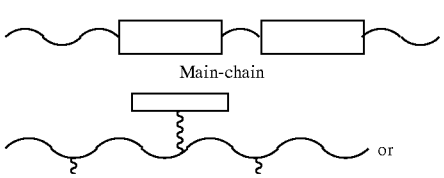

Main-chain

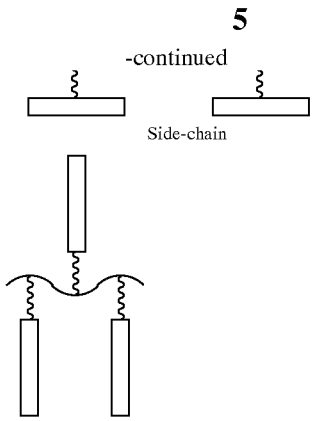
Side-chain

The side chain liquid crystal polymer can generally be thought of as containing a flexible polymer with rigid segments (the mesogenic unit) attached along its length by short flexible (or rigid) units. It is the anisotropic, rigid section of the mesogenic units that display orientational order in the liquid crystal phases. In order to affect the phases exhibited by the liquid crystal and the subsequent optical properties there are many features which can be altered, some of these features are particularly pertinent to side-chain liquid crystal polymers. One of these features is the flexible part that joins the mesogenic unit to the polymer backbone which is generally referred to as the spacer group. The length and flexibility of this spacer group can be altered.

A number of side-chain liquid crystal polymers are known, for example see GB 2146787 A.

Liquid crystal polyacrylates are a known class of liquid crystal polymer (LCP). LCPs are known and used in electro-optic applications, for example in pyroelectric devices, non-linear optical devices and optical storage devices. For example see GB 2146787 and Makromol. Chem. (1985) 186 2639–47.

Side-chain liquid crystal polyacrylates are described in Polymer Communications (1988), 24, 364–365 e.g. of formula:

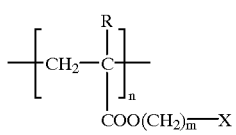

where $(CH_2)_m$ is the flexible spacer group and X is the side-chain mesogenic unit and R is hydrogen or alkyl.

Side-chain liquid crystal polychloroacrylates are described in Makromol. Chem. Rapid Commun. (1984), 5, 393–398 e.g. of formula:

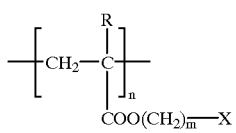

where R is chlorine.

Patent Application PCT GB 94/00662 describes amongst other things the use of the Baylis-Hillman Reaction to make a range of novel liquid crystal polymers.

A method for the preparation of polyacrylate homo- or co-polymers having the following repeat unit is described in UK patent application GB 9203730.8

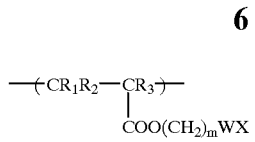

$R_1$ and $R_2$ are independently alkyl or hydrogen, $R_3$ is alkyl, hydrogen or chlorine, m is 0 or an integer 1–20, W is a linkage group COO or OOC or O and X is a mesogenic group.

One of the main problems with liquid crystal polymers is that they are extremely difficult to align in devices. Essentially there are two techniques which have been used for aligning liquid crystal polymers. It is possible to try to align the liquid crystal polymer in a similar manner as a low molar mass liquid crystal, which is described in more detail below. Alternatively, mechanical techniques can be used such as shearing. Typically mechanical shearing is performed over hot rollers, this technique is generally only suitable for flexible substrates. It is possible to shear a sample between glass slides however the glass slides cannot be sealed in the conventional manner.

Materials and Assembling Process of LCDs by Morozumi in Liquid Crystals Applications and uses, vol. 1 Ed. Bahadur, World Scientific Publishing Co, Pte. Ltd, 1990 pp 171–194 and references therein as the title suggests discusses methods for assembling liquid crystal devices.

The technique for aligning low molar mass liquid crystals is typically as follows. Transparent electrodes are fabricated on the surfaces of the substrates, the substrates typically being made of glass e.g. glass slides. In twisted nematic or super twisted nematic devices, for example, an alignment process is necessary for both substrates. A thin alignment layer is deposited to align the liquid crystal molecules, typically either organic or inorganic aligning layers are used, for example SiO deposited by evaporation is a typical inorganic alignment layer. One method to form the alignment layer involves rubbing the surface by textures or cloths. Polyimides have also been employed for the surface alignment of layers. Polyimide is coated onto the substrates bearing electrodes by a spinner and then cured to form a layer of approximately 50 nm thickness. Then each layer surface is repeatedly rubbed in substantially one direction with an appropriate material. If the liquid crystal molecules are deposited on this layer they are automatically aligned in the direction made by the rubbing. It is often preferable if the molecules possess a small angle pre-tilt typically 2–3°. Higher pre-tilts are sometimes required.

The two substrates are then fixed together for example by adhesive and are kept separate by spacing materials. This results in uniform and accurate cell spacing. A typical adhesive is an epoxy resin. This sealing material is usually then precured. The electrodes may then be precisely aligned for example to form display pixels. The cell is then cured at, for example 100–150° C. At this point the empty liquid crystal cell is complete.

It is at this point that the cell is filled with the liquid crystal material. The opening size in the sealing area of the liquid crystal cell is rather small therefore the cell can be evacuated, for example in a vacuum chamber, and the liquid crystal material forced into the cell via gas pressure. More than one hole in the sealing area may be used. The empty cell is put into a vacuum chamber and then the vacuum chamber is pumped down. After the cell has been evacuated the open region of the sealant is dipped into the liquid crystal material and the vacuum chamber is brought back to normal pressure. Uquid crystal material is drawn into the cell as a result of capillary action, external gases can be applied to increase the pressure. When the filling process is complete the hole or holes in the sealant is/are capped and the cell is cured at a temperature above the liquid crystal material clearing point to make the liquid crystal molecular alignment stable and harden the capping material.

Polymer liquid crystal molecules tend to be more viscous than low molecular weight liquid crystal materials and are therefore more difficult to align and more difficult to fill into devices. Only liquid crystal polymers with low molecular weights can be flow filled into a cell, and once a degree of polymerisation greater than around 30 or 40 repeat units is reached, most liquid crystal polymers become so viscous that flow filling cells is extremely difficult. Much slower cooling is needed in order to try and align liquid crystal polymers and this usually results in poor uniformity of alignment.

Poorly aligned liquid crystal molecules do not result in the fast switching high contrast materials and devices that are generally required.

The above techniques are suitable for many liquid crystal materials including those devices which use liquid crystal materials which exhibit and utilise the smectic mesophase e.g. ferroelectrics. Suitable alignment techniques may also be found in GB 2210469 B. Devices containing ferroelectric liquid crystal mixtures can exhibit fast switching times (faster than 100 ms), Clark and Lagerwall, Appl. Phys. Lett., 36, 89, 1980. They can be bistable which means that they can be multiplexed at high levels using a line-at-a-time scan technique. Ferroelectric materials continue to receive a large amount of investigative attention due to their application in high resolution flat panel displays. An important feature of devices containing liquid crystalline materials is that they should exhibit a fast response time. The response time is dependent on a number of factors, one of these being the spontaneous polarisation, denoted Ps (measured in nC cm$^{-2}$). By adding a chiral dopant to the liquid crystalline mixture the value of Ps can be increased, thus decreasing the response time of the device. Ferroelectric smectic liquid crystal materials, which can be produced by mixing an achiral host and a chiral dopant, use the ferroelectric properties of the tilted chiral smectic C, F, G, H, I, J, and K phases. The chiral smectic C phase is denoted $S_C^*$ with the asterisk denoting chirality. The $S_C^*$ phase is generally considered to be the most useful as it is the fastest switching. It is desirable that the material should exhibit a long pitch chiral nematic (denoted N*) and $S_A$ phase at temperatures above the chiral smectic phase in order to assist surface alignment in a device containing liquid crystalline material. Ferroelectric smectic liquid materials should ideally possess the following characteristics: low viscosity controllable Ps and an $S_C^*$ phase that persists over a broad temperature range, which should include ambient temperature, and exhibits chemical and photochemical stability. Materials which possess these characteristics offer the prospect of very fast switching liquid crystal containing devices.

Ferroelectric LCDs by Dijon in Liquid Crystals Applications and Uses, vol. 1 Ed. Bahadur, World Scientific Publishing Co. Pte. Ltd, 1990 pp 350–360 and references therein discusses alignment processes for smectic phases for low molar mass materials. The filling of cells is believed to be possible only in the isotropic or nematic phase due to the viscosity of smectic phases. Generally materials with the following phase sequence give good alignment:

$$I\text{---}N^*\text{---}S_A\text{---}S_C^* \text{ or } I\text{---}S_A\ S_C^*$$

whereas materials with the following phase sequences are more difficult to align:

$$I\text{---}N^*\text{---}S_C^*$$

Typically, therefore, in order to use a liquid crystal material in the smectic phase it will involve heating the material to the nematic or isotropic phase and allowing it to cool slowly into an aligned smectic state. Should this technique be applied to a polymer liquid crystal material then the cooling time is usually very much longer in order to assist the alignment, though very often the alignment is poor.

Another class of materials which may contain liquid crystal properties are mesogenic substituted organosilsesquixanes. For example see European patent application 0446 912 A1. Other references include European patent applications 0348705, 0367222, 0163495A3 and Makromol. Chem., Macromol. Symp., 50, 215–228, 1991.

There is a continued need for new liquid crystal materials which possess the properties that allow them to be used in devices including one or more of the known electro-optic devices.

BRIEF DESCRIPTION OF THE DRAWINGS

FIG. 2 is a cross-sectional view of a liquid crystal device in which the materials of the invention may be incorporated;

FIG. 3 is a cross-sectional view of a pyroelectric detector device in which the materials of the invention may be incorporated;

DESCRIPTION OF THE INVENTION

Figure 1:
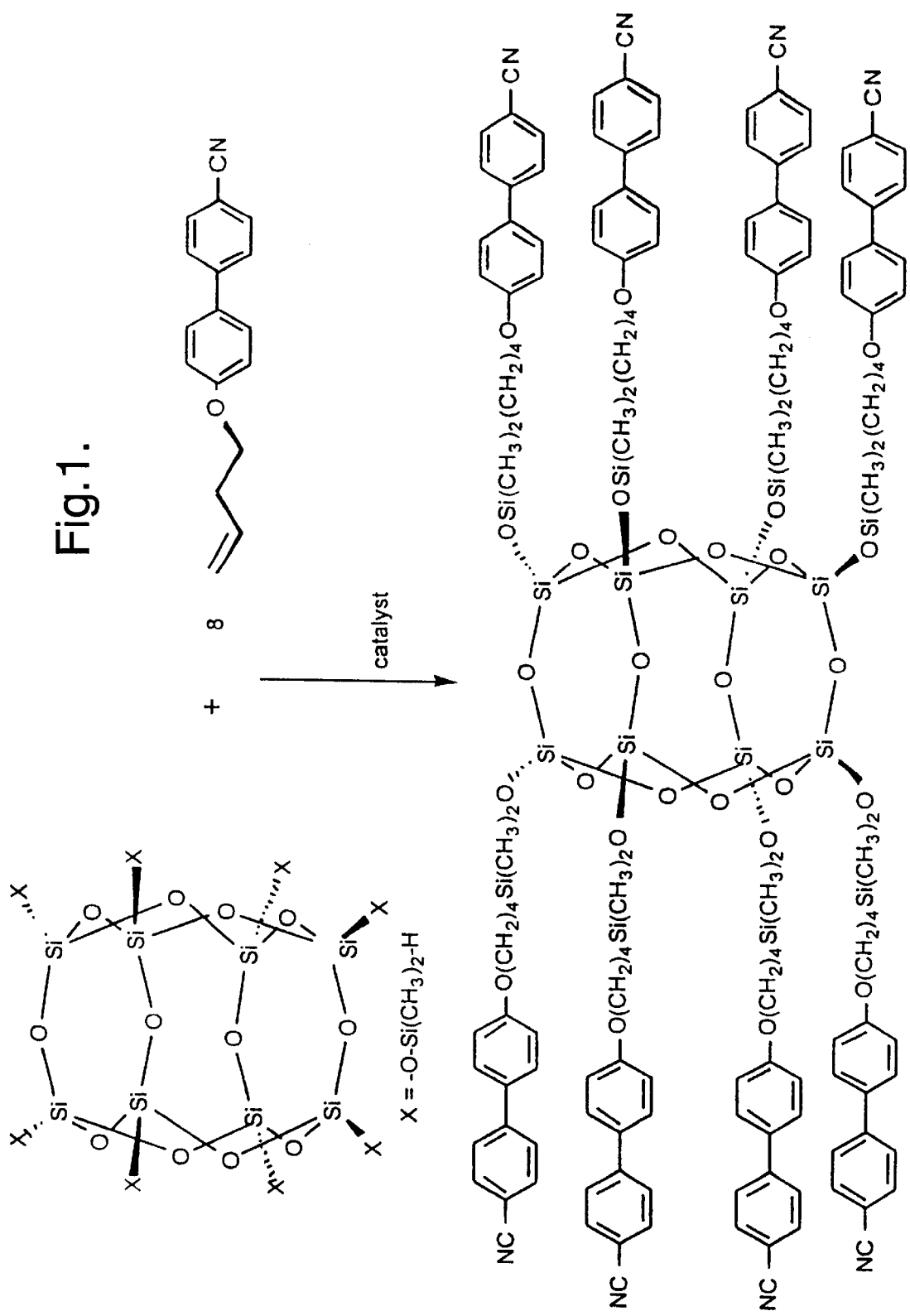
FIG. 1 is a synthetic scheme for preparing compounds of the invention.

According to this invention there is provided a material of general formula I:

$$[G]_g(SiO_{1/2})_x \qquad\qquad I$$

wherein G is $R_3SiR_1R_2(O)_k$;

$R_1$, $R_2$, $R_3$ are independently selected from $C_{1-16}$ alkyl which may be partly or fully halogenated, H and formula IA:

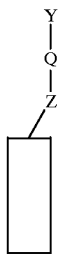

IA wherein Y is selected from COO, OCO, O, S, CHOH, CHF, $CH_2$;

$Q=(CH_2)_n$ wherein one or more non-adjacent methylenes may be replaced by O and n=1–20;

Z is selected from O, S, single covalent bond, COO, OCO;

when Y is CH$_2$ then n may also be 0;

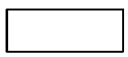

represents any mesogenic group;
provided that at least one of R$_1$, R$_2$, R$_3$ is selected from formula IA;
k=0 or 1; g=4 or 6 or 8 or 10 or 12; I=3 or 8 provided that:
if k=1, I=3 and x is selected from 6,8,10,12 then g=x;
if k=0, I=8 and g=4 then x=1;
and further provided that G may have up to g different structures for any single compound.

The mesogenic group may be further defined from general structure II

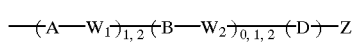

II

A, B, D are independently selected from the following rings:

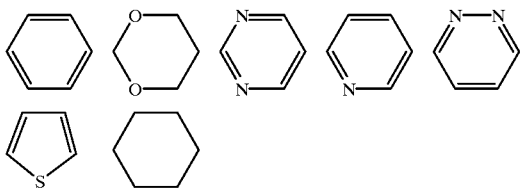

the above rings may be substituted with one or more of the following substituents in at least one of the available substitution positions: F, Cl, Br, CH$_3$, CN, OR, R and NCS where R is given by C$_{1-5}$ branched or straight chain alkyl;
Z is selected from CN, F, Cl, NO$_2$, R, OR, CO$_2$R, CF$_3$, OOCR, NCS, SCN, where R=straight chain or branched chain alkyl and may include from 1–16 carbon atoms and including where one or more non-adjacent CH$_2$ groups may be substituted by CH(CN), CH(CF$_3$), CH(Cl), CH(CH$_3$) in chiral or non-chiral form;
provided that the total number of rings present is not greater than 4;
W$_1$ and W$_2$ are independently selected from COO, OCO, single bond, CH$_2$CH$_2$, CH$_2$O, OCH$_2$, O, S, CH=CH, C≡C, N=N.

In a further aspect of the invention one or more of the groups R$_1$, R$_2$, R$_3$ may possess a polymerisable group, such that the compounds of formula I may be polymerised to form liquid crystal polymers. Polymerisable groups include double bonds and triple bonds and epoxide groups.

Preferably R$_1$, R$_2$, R$_3$ are all selected from Formula IA.
Preferably when any of R$_1$, R$_2$, R$_3$ are selected from C$_{1-16}$ alkyl when it is partly or fully halogenated, the halogen group is selected from F or Cl.
Preferably x is selected from 4,6,8,10.
Preferably Y is CH$_2$.
Preferably Z=O, CO$_2$ or single covalent bond.

There are various catalysts which may be used in the synthetic procedure, for example Platinum metals and/or compounds of platinum metals. These include Platinum, Palladium, Rhodium and Iridium and alloys containing such compounds consisting at least of one of the platinum metals and chemical compounds containing platinum metals and mixtures of them.

Preferred is platinum itself, its chemical derivatives and its alloys, which may be bonded or deposited on a supporting structure. All catalysts may be used which have been used for the addition of unsaturated aliphatic materials to hydrogen atoms bonded to Si atoms.

Examples of such catalysts are metallic and finely dispersed platinum, which can be situated on supports such as silicon dioxide, aluminium oxide or charcoal. Further examples are derivatives or complexes of platinum for example PtCl$_4$, Na$_2$PtCl$_4$*4H$_2$O, H$_2$PtCl$_6$*6 H$_2$O (Speier's catalyst), platinum-olefin complexes, platinum-alkanol complexes, platinum-alkanolate complexes, platinum-ether complexes, platinum-aldehyde complexes, platinum-ketone complexes, including reaction products of H$_2$PtCl$_6$ and cyclohexanone, Platinum-vinylsiloxane complexes especially platinum-divinylssiloxane complexes with or without the presence of detectable inorganically bonded halogen, platinum-divinyl tetraethyidisiloxane complex in xylene as disclosed in B. D. Karstedt, U.S. Pat. No. 3,814,730), 1974), available from Fluorochem Ltd, bis-(gamma-picolin)-platinum dichloride, trimethylene-dipyridine-platinum-dichloride, dicyclopentdieneplatinum-chloride, dimethyl-sulfoxydiethylen platinum-(II)-dichloride as well as reaction products of platinum tetrachloride with olefin and primarary amine or secondary amine or primary amine and secondary amine as well as the reaction product of platinum tetrachloride dissolved in 1-octene with sec. butylamine.

The platinum catalyst is used preferentially in amounts of 0.2 to 1000 ppm (by weight) (amount of weight per million amounts of weight) calculated as the amount of weight of the elemental platinum relative to the amount of weight of the reactant side chain given in FIG. 1.

Reaction conditions refer to the coupling of the siloxane core to the mesogenic group. The reaction temperature is chosen between the melting temperature of the solvent or the solvent mixture and its boiling temperature, approximately 110° C. in the case of toluene.

For the synthesis of materials with a structure commonly described as a cage (D. Hoebbel, W. Wieker, Z. anorg. allg. Chem., 1971, 384, 43; D. Hoebbel, G. Garzó, G. Engelhardt, E. Lippma, M. Alla, Z. anorg. allg. Chem., 1980, P. G. Harrison, R. Kannengiesser, J. Chem. Soc. Chem. Commun. 1996, 415, reviewed in R. H. Baney, M. Itoh, A. Sakakibara, T. Suzuki, Chem Rev. 1995, 95, 1409) reaction temperatures between 4 to 40° C. in toluene as solvent with Karstedt's catalyst as catalyst show from the viewpoint of ease of synthesis the best results, if the aim is the avoidance of side reactions of the silicone atoms of the cage.

The reaction can be carried out in the absence or in the presence of a solvent. The term solvent does not mean that the reaction components have to be dissolved completely. The reaction can be carried out in suspension or emulsion of one or more of the reaction components. From the viewpoint of the ease of production inert organic solvents show the most desirable performance.

The solvent can be chosen from a common solvent or a mixture of common solvents. Examples of solvents are: alkanols e.g. methanol, ethanol, n-propanol, iso-propanol, n.-, sec. and tert. butanol, ester e.g. methylacetate, ethylacetate, n-. and iso propylacetate, n-. and sec. and tert. butylacetate, ethylformiate, diethylcarbonate, ether e.g diethylether, tetrahydrofuran, dioxan, di-n-propylether, di-n-butylether and anisol, cresol, chlorinated hydrocarbons e.g. dichloromethane, trichloromethane, tetrachloromethane, 1,2 dichloromethane, 1,1,1-trichloroethane, trichloroethylene, chlorobenzene, hydrocarbons e.g. pentane, n-hexane, cyclohexane, isomer mixtures of hexane, isomer mixtures of heptane, octane, isomer mixtures of octane, mixtures of different alkanes known as petrol ethers, benzene, toluene, xylene or mixtures thereof can be used. Preferentially solvents like dichloromethane, benzene, tetrahydrofuran, diethylether and toluene and mixtures thereof are used.

The coupling reaction between the siloxane core and the mesogenic group can be carried out at ambient pressure, this means at approximately 0.1 MPa (abs.) or at pressures of 0.01 to 0.5 MPa (abs.).

The reaction can be carried out in the presence of $O_2$ as outlined by L. N. Lewis et al. *J. Am. Chem. Soc.*, 1990, 112, 5998 or by M. Moran, C. M. Casado, I. Cuadrodo, J. Losada, *Organometallics*, 1993, 12, 4327; or equally in the absence of $O_2$.

The final products of the invention may be obtained by the reaction of $(G)_g(SiO_{1/2})_x$ given in the general formula 1 when at least one of the groups of $(G)_g$ contains a component Si—H, with a material of the general formula 1A, providing at least one unsaturated aliphatic group is present. Preferably the unsaturated group is a terminal group and is in the position Y of formula IA.

The liquid crystalline organosilicone compounds of the invention may be prepared by dissolving a material containing at least one SiH group and materials containing double bonds and liquid crystalline groups in a solvent together with a platinum catalyst or a solvent mixture.

The materials can be synthesised according to the following procedures.

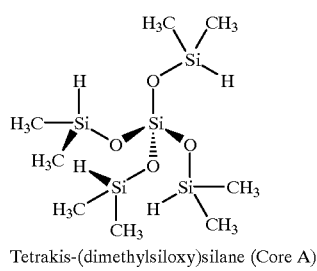

Tetrakis-(dimethylsiloxy)silane (Core A)

Core A can be obtained by a method outlined in EP 01 63495 or alternatively it is commercially available from Fluorochem Ltd., Old Glossop, Derbyshire, UK.

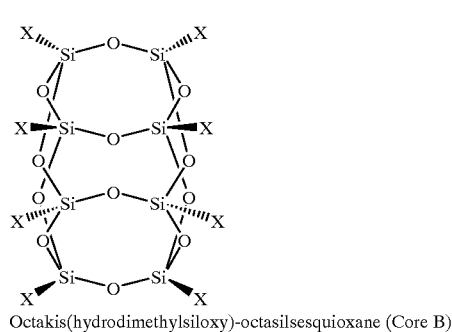

Octakis(hydrodimethylsiloxy)-octasilsesquioxane (Core B)

X = —O—Si(CH$_3$)$_2$—H

Synthesis of Octakis(hydrodimethylsiloxy)-octasilsesquioxane, Core B.

Tetramethylammoniumsilicate (4.7 g, 0.05 mol) was added as a 10% aqueous solution to a solution of heptane (100 ml), dimethylformamide (200 ml) and dimethylchlorosilane (100 ml) which had been previously stirred for 20 min. The weakly exothermic reaction was then cooled slowly to 4° C., and 1 l of water, at the temperature of 4° C., was added slowly. The organic phase was separated from the aqueous phase and then washed with water until acid free. The organic solution was concentrated by evaporation under reduced pressure, and resulting mixture was cooled to 4° C. in order to facilitate the precipitation of octakis (hydrodimethylsiloxy)-octasilsesquioxane as a white solid, which was isolated after purification by recrystallisation from acetone; yield 1.48 g (73.8%). ν(KBr disc) (cm$^{-1}$): 2960 (C—H), 2142 (Si—H), δ$_H$(270 MHz, CDCl$_3$) (ppm): 4.7 (1H, s, Si—$\underline{H}$), 0.2 (6H, s Si—C$\underline{H}_3$), δ$_{Si}$(53.5 MHz, CDCl$_3$) (ppm): )0.5 (H—$\underline{Si}$—CH$_3$), -108.8 ($\underline{Si}$—(O)$_4$—).

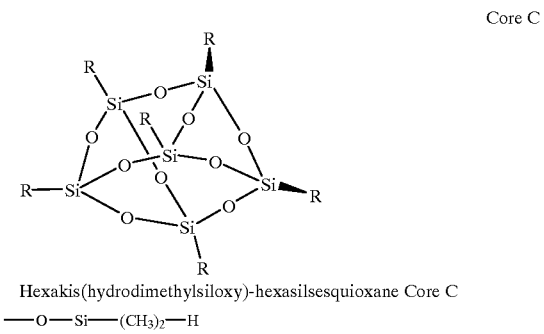

Hexakis(hydrodimethylsiloxy)-hexasilsesquioxane Core C

R = —O—Si—(CH$_3$)$_2$—H

Synthesis of Core C

Synthesis of the tetraethylammoniumsilicate 113 g tetraethoxysilane was added dropwise to a solution consisting of 206 g 40% aqueous solution of tetraethylammoniumhydroxide (Fluka Chemicals, Gillingham, UK) and 100 ml water. The reaction mixture was stirred for 24 h at room temperature. The solvent was removed in vacuo at room temperature and the residue was crystallised at 4° C.

Sylilation 22 g of the tetraethylammoniumsilicate are added slowly to a solution kept at 4° C. consisting of dimethylformamide (80 ml), heptane (80 ml) and dimethylchlorosilane 80 ml (69.1 g). During the addition the temperature of the reaction mixture rose to 12° C. Subsequently heptane 200 ml was added and the organic phase was washed with water until the aqueous phase was found to be neutral. The organic phase was dried over Na$_2$SO$_4$ filtered and the solvent was removed in vacuo. At 4° C. the slow formation of crystals was found. The first crop yielded after 60 days 0.4 g (5% yield). ν(KBr disc) (cm$^{-1}$): 2960 (C—H), 2142 (Si—H), d$_H$(270 MHz, CDCl$_3$) (ppm): 4.8 (1H, s, Si—$\underline{H}$), 0.2 (6H, s Si—C$\underline{H}_3$), δ$_{Si}$(53.5 MHz, CDCl$_3$) (ppm):) 0.5 (H—$\underline{Si}$—CH$_3$), -98.3 ($\underline{Si}$—(O)$_4$—). The spectroscopic and analytic data are in line with the proposed structure of Hexakis (hydrodimethylsiloxy)-hexasilsesquioxane Core C.

Synthesis of the side chains.

The synthetic methods by which the following sidechains can be obtained are commonly known in the field of liquid crystals and have been outlined in *Side Chain Liquid Crystals*, Ed. C. B. McArdle, Blackie, London, 1989, *Ferroelectric Liquid Crystals*, Ed. J. W. Goodby, Gordon and Breach Science Publishers, Philadelphia and in the references therein.

n = 1, 3, 8
For n = 1 Sidechain 1
For n = 3 Sidechain 2
For n = 8 Sidechain 3

Sidechain 4

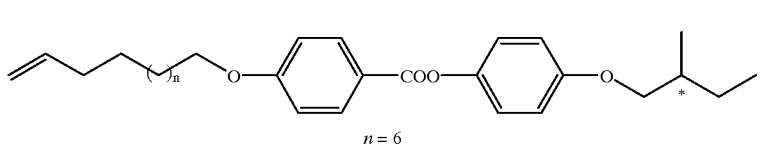

n = 6

Sidechain 5

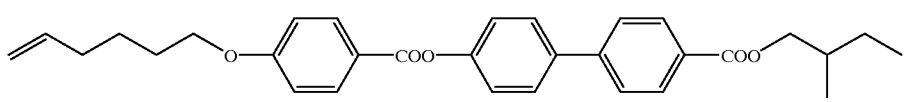

Sidechain 6

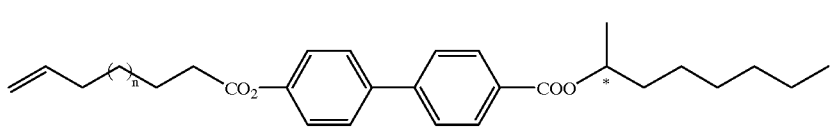

n = 5

Sidechain 7

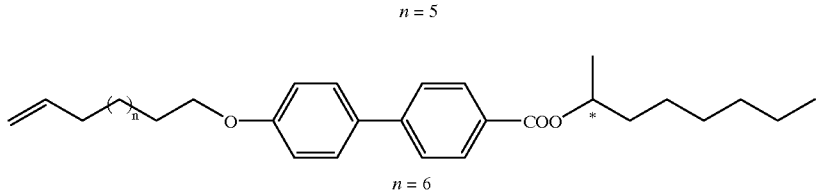

n = 6

Sidechain 8

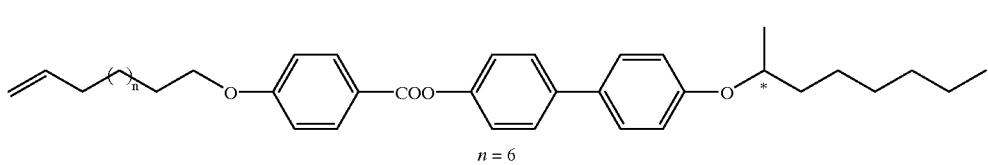

n = 6

Sidechain 9

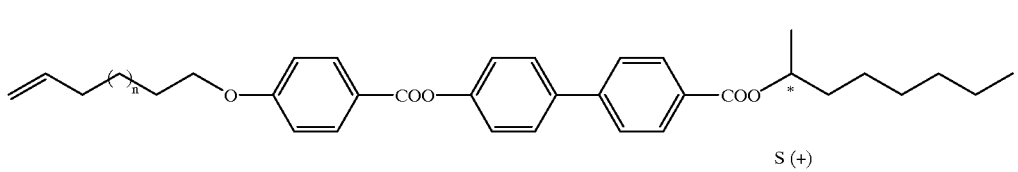

S (+)

n = 6

The properties of the following examples are given:

| Examples | Core | Sidechains |
|---|---|---|
| 1 | B | 1 |
| 2 | B | 2 |
| 3 | B | 3 |
| 4 | A | 4 |
| 5 | B | 4 |
| 6 | A | 5 |
| 7 | B | 5 |
| 8 | C | 5 |

Synthesis of Octakis(4-cyano-4'-(6-dimethylsiloxy) hexyloxy-biphenyl)-octasilsesquioxane Example 2.

A solution of toluene (20 ml), sidechain 2 (4-cyano-4'-(5-hexenyloxy)biphenyl)) (0.55 g, 1.58 mmol) and 10 ml of a 3.0–3.5% solution of Karstedt's catalyst dissolved in xylene was prepared. The solution was gently aerated for 20 secs, and then a solution of octakis(hydrodimethylsiloxy)-octasilsesquioxane (0.1g, 0.098 mmol) in dry toluene (10 ml) was added dropwise at room temperature over a period of 1 h. A few minutes after the addition was complete no Si—H band (2142 $cm^{-1}$) could be detected by IR-spectroscopy. A spatula tip of triphenylphosphine was added in order to convert the catalyst to the less reactive triphenylphosphine complex and the solution was concentrated under reduced pressure. The oligomeric material was isolated via precipitation in methanol. The product was separated by filtration, and purified by repetitive precipitation from methanol until no monomer could be detected by chromatographic methods. Recrystallisation from pentane yielded 0.31 g of 2 (85% yield). Spectral data: n(KBr disc) ($cm^{-1}$): 3020 (Ar—H), 2940 (C—H), 2220 (C≡N), 1600 (Ar), 860 (C—H); $d_H$(270 MHz, $CDCl_3$) (ppm): 7.65 (4H, m, Ar—H), 7.52 (2H, m, Ar—H), 6.95 (2H, m, Ar—H), 3.93 (2H, tr, Ar—O—$CH_2$), 1.75 (2H, m, O—$CH_2$—$CH_2$—), 1.45 (6H, m, $CH_2$—$CH_2$—$CH_2$), 0.62 (2H, tr, $CH_2$—Si), 0.14 (6H, s, ($CH_3$—Si); $d_C$ (67.8 MHz, $CDCl_3$) (ppm): 0.01

($\underline{C}H_3$—Si), 18.14 ($\underline{C}H_2$—Si), 23.49, 26.31, 24.78, 33.75, (CH$_2$—$\underline{C}H_2$—CH$_2$), 110.82 (Ar. C$_{4'}$, $\underline{C}$—CN), 115.19 (Ar. C$_3$, C$_5$), 126.89, 128.48 (Ar. C$_2$, C$_6$, C$_{2'}$, C$_{6'}$), 131.56 (Ar. C$_1$), 132.49 (Ar. C$_{3'}$, C$_{5'}$), 144.71 (Ar. C$_{1'}$), 160.11 (Ar. C$_4$, O—C), 118.87 ($\underline{C}$—N); d$_{Si}$(53.5 MHz, CDCl$_3$) (ppm): 12.34 (Si—CH$_3$), -108.8 ($\underline{Si}$—(O)$_4$—).The spectroscopic and analytic data are in line with the proposed structure of an intact Core B.

Synthesis of Example 6

A solution of side chain 5 (0.5 g, 1.03 mmol), 3.0–3.5% solution of Karstedt's catalyst available from Fluorochem in xylene (3 μl) and toluene (15 ml) was prepared. A gentle stream of air was blown through the solution for 20 seconds. A solution of core A (tetrakis-(dimethylsiloxy)silane) (0.067 g, 0.20 mmol) (available from Fluorochem) in dry toluene was added dropwise at room temperature over a period of 1 h. During this time the solution, which was originally colourless, developed a faint yellowish colour. The reaction was monitored by IR spectroscopy. A few minutes after completion of the addition of the monomer no Si—H absorption could be detected by IR-spectroscopy. A spatula tip of triphenylphosphine was added and the solution was concentrated under reduced pressure. The oligomeric material was purified by precipitation into methanol. The product was separated by filtration. The process of consecutively dissolving and precipitating the product with methanol was repeated until the remaining starting monomer could not be detected by chromatographic methods. After drying in vacuo the product was collected as a white tacky substance in a yield of 0.28 g (61 percent). The absence of a peak in the vicinity of 2.1 ppm in the $^1$H-NMR spectrum shows that no β-addition of the olefins had taken place, and that the oligomeric materials were therefore single compounds.

Synthesis of Example 8

A solution of side chain 5 (0.18 g, 0.37 mmol), 3.0–3.5% solution of Karstedt's catalyst available from Fluorochem in xylene (3 μl) and toluene (15 ml) was prepared. A gentle stream of air was blown through the solution for 20 seconds. A solution of Core C (hexakis(hydrodimethylsiloxy)-hexasilsesquioxane) (0.040 g, 0.05 mmol) in dry toluene was added dropwise at room temperature over a period of 1 h. During this time the solution, which was originally colourless, developed a faint yellowish colour. The reaction was monitored by IR spectroscopy. A few minutes after completion of the addition of the monomer no Si—H absorption could be detected by IR-spectroscopy. A spatula tip of triphenylphosphine was added and the solution was concentrated under reduced pressure. The oligomeric material was purified by precipitation into methanol. The product was separated by filtration. The process of consecutively dissolving and precipitating the product with methanol was repeated until the remaining starting monomer could not be detected by chromatographic methods. After drying in vacuo the product was collected as a white substance in a yield of 0.1 g (68 percent). The absence of a peak in the vicinity of 2.1 ppm in the $^1$H-NMR spectrum shows that no β-addition of the olefins had taken place, and that the oligomeric materials were therefore single compounds. The spectroscopic and analytic data are in line with the proposed structure of an intact Core C.

| Example | silicone core | Side Chain | Tg (° C.) {ΔCp (J g$^{-1}$ K$^{-1}$)} | Transitions (° C.) {ΔH (J g$^{-1}$)} |
|---|---|---|---|---|
| 1 | B | 1 | 11.0 {0.22} | S$_A$ 93.9 {4.31} Iso |
| 2 | B | 2 | 3.0 {0.32} | S$_1$ 22.5 {0.19} S$_A$ 116.5 {5.40} Iso |
| 3 | B | 3 | -7.5 {0.28} | cr 34.4 {10.2}S$_2$ 54.6 {0.77} S$_3$ 64.5 {1.20}S$_A$ 128.5 {8.66} Iso |
| 4 | A | 4 | — | S$_1$ 22.7 S$_{Calt}$ 68.2 Iso |
| 5 | B | 4 | 0.6 | S$_C$ 85.8 S$_A$ 96.2 Iso |
| 6 | A | 5 | -8.4 {0.47} | S$_{Calt}$ 125.0 S$_C$ 154.4 S$_A$ 188.7 Iso |
| 7 | B | 5 | — | Cr 143.0 S$_C$ 208.0 S$_A$ 214.0 Iso |
| 8 | C | 5 | 11.2 {0.14} | S$_C$ 190.5 {1.30} Iso |

The denomination S$_1$, S$_2$, S$_3$ refer to unknown smectic phases the denomination S$_{Calt}$ to an alternating (commonly known as anticlinic)S$_C$ phase.

Some of the compounds described by the current invention exhibit antiphases. The materials of the present invention may be usefully employed in antiferroelectric devices. An example of the use of a material and device embodying the present invention will now be described with reference to FIG. 2.

The liquid crystal device consists of two transparent plates, 1 and 2, for example made from glass. These plates are coated on their internal face with transparent conducting electrodes 3 and 4. An alignment layer 5,6 is introduced onto the internal faces of the cell so that a planar orientation of the molecules making up the liquid crystalline material will be approximately parallel to the glass plates 1 and 2. This is done by coating the glass plates 1,2 complete with conducting electrodes so that the intersections between each column and row form an x, y matrix of addressable elements or pixels. For some types of display the alignment directions are orthogonal. Prior to the construction of the cell the layers 5,6 are rubbed with a roller covered in cloth (for example made from velvet) in a given direction, the rubbing directions being arranged parallel (same or opposite direction) upon construction of the cell. A spacer 7 e.g. of polymethyl methacrylate separates the glass plates 1 and 2 to a suitable distance e.g. 2 microns. Liquid crystal material 8 is introduced between glass plates 1,2 by filling the space in between them. This may be done by flow filling the cell using standard techniques. The spacer 7 is sealed with an adhesive 9 in a vacuum using an existing technique. Polarisers 10, 11 may be arranged in front of and behind the cell.

Alignment layers may be introduced onto one or more of the cell walls by one or more of the standard surface treatment techniques such as rubbing, oblique evaporation or as described above by the use of polymer aligning layers.

In alternative embodiments the substrates with the aligning layers on them are heated and sheared to induce alignment, alternatively the substrates with the aligning layers are thermally annealed above the glass transition temperature and below the liquid crystal to isotropic phase transition in combination with an applied field. Further embodiments may involve a combination of these aligning techniques. With some of these combinations an alignment layer may not be necessary.

The device may operate in a transmissive or reflective mode. In the former, light passing through the device, e.g. from a tungsten bulb, is selectively transmitted or blocked to form the desired display. In the reflective mode a mirror, or diffuse reflector, (12) is placed behind the second polariser 11 to reflect ambient light back through the cell and two polarisers. By making the mirror partly reflecting the device may be operated both in a transmissive and reflective mode.

The alignment layers 5,6 have two functions, one to align contacting liquid crystal molecules in a preferred direction and the other to give a tilt to these molecules—a so called surface tilt—of a few degrees typically around 4° or 5°. The alignment layers 5,6 may be formed by placing a few drops of the polyimide on to the cell wall and spinning the wall until a uniform thickness is obtained. The polyimide is then cured by heating to a predetermined temperature for a predetermined time followed by unidirectional rubbing with a roller coated with a nylon cloth.

In an alternative embodiment a single polariser and dye material may be combined.

The liquid crystal material 8 when introduced into the cell may consist of liquid crystal material given by formula I which may include liquid crystal polymers made from compounds of formula 1. Should the intertion be to incorporate liquid crystal polymers in to the cell then the material 8 may consist of liquid crystal monomers and a photoinitiator. It may also contain a reagent which will limit the molecular weight of the polymer for example a chain transfer reagent and it may also include a thermal initiator.

The monomer material may be aligned before polymerisation using standard techniques, for example by heating up to and cooling from the isotropic phase or from a liquid crystal phase such as a nematic or chiral nematic phase. It is also possible that the liquid crystal polymer may be aligned by one or more techniques including the use of surface forces, shear alignment or field alignment.

It is possible that following polymerisation there may still be some amount of monomer material remaining. This may be unreacted monomer or low molar mass additives which do not bear polymerisable groups.

Polymerisation may be carried out by using any of the known techniques. For example the monomer material plus initiator may be exposed to UV light, heat may also be applied to permit polymerisation within a given phase of the monomer and/or polymer.

Alternatively the polymerisation process may take place in the presence of heat and a thermal initiator. However if this technique is used it may be preferable if it is carried out at a temperature which corresponds to a liquid crystal phase of the monomer material.

In-situ polymerisations are described in UK Patent Application GB 9420632.3 which also describes the use of chain transfer reagents to control molecular weight of liquid crystal polymers. As mentioned above there may also be a chain transfer reagent present in the mixture of the current invention. GB 9514970.4 describes in-situ polymerisations in the presence of a cationic photoinitiator.

Many of the compounds described by formula I and mixtures including compounds of formula I show liquid crystalline behaviour and are thus usefully employed in liquid crystal devices. Example of such devices include optical and electro-optical devices, magneto-optical devices and devices providing responses to stimuli such as temperature changes and total or partial pressure changes. The compounds of formula I may also be included in a mixture, where the mixture comprises at least two compounds. Typical mixtures include mixtures consisting of compounds of formula I and also mixtures comprising at least one compound of formula I and at least one compound not of formula I.

Materials have been proposed for laser addressed applications in which laser beams are used to scan across the surface of the material or leave a written impression thereon. For various reasons many of these materials have consisted of organic materials which are at least partially transparent in the visible region. The technique relies upon localised absorption of laser energy which causes localised heating and in turn alters the optical properties of the otherwise transparent material in the region of contact with the laser beam. Thus as the beam traverses the material, a written impression of its path is left behind. One of the most important of these applications is in laser addressed optical storage devices, and in laser addressed projection displays in which light is directed through a cell containing the material and is projected onto a screen. Such devices have been described by Khan Appl. Phys. Lett. vol. 22, p111, 1973; and by Harold and Steele in Proceedings of Euro display 84, pages 29–31, September 1984, Paris, France, in which the material in the device was a smectic liquid crystal material. Devices which use a liquid crystal material as the optical storage medium are an important class of such devices. The use of semiconductor lasers, especially $Ga_xAl_{1-x}$ As lasers where x is from 0 to 1, and is preferably 1, has proven popular in the above applications because they can provide laser energy at a range of wavelengths in the near infra-red which cannot be seen and thus cannot interfere with the visual display, and yet can provide a useful source of well-defined, intense heat energy. Gallium arsenide lasers provide laser light at wavelengths of about 850 nm, and are useful for the above applications. With increasing Al content (x<1), the laser wavelength may be reduced down to about 750 nm. The storage density can be increased by using a laser of shorter wavelength.

The compounds of the present invention may be suitable as optical storage media and may be combined with dyes for use in laser addressed systems, for example in optical recording media.

The smectic and/or nematic properties of the materials described by the current invention may be exploited. For example the materials of the present invention nay be used in ferroelectric mixtures and devices.

The compounds of the present invention may also be used in pyroelectric devices for example detectors, steering arrays and vidicon cameras.

FIG. 3 illustrates a simple pyroelectric detector in which the materials of the present invention may be incorporated.

A pyroelectric detector consists of electrode plates 13,14 at least one of which may be pixellated. In operation the detector is exposed to radiation R, for example infrared radiation, which is absorbed by the electrode 13. This results in a rise in temperature which is transmitted to a layer of pyroelectric material 15 by conduction, The change in temperature results in a thermal expansion and a charge is generated. This change in charge is usually small when compared with the charge output due to the change in the spontaneous polarisation, Ps with a change in temperature; this constitutes the primary pyroelectric effect. A change in charge results in a change in potential difference between the electrodes. The charge on each pixel may be read out and the resulting signal is used to modulate scanning circuits in, for example, a video monitor and for a visual image of the infra red scans.

The selective reflective properties of the materials described by the current invention may also allow for materials of the current invention to be used in inks and paints and they may therefore be useful in anti-counterfeiting operation. They may also be used in so-called security inks. Other applications include thermal control management, for example the materials may be included in a coating which may be applied to one or more windows in order to reflect infra-red radiation.

Figure 4:
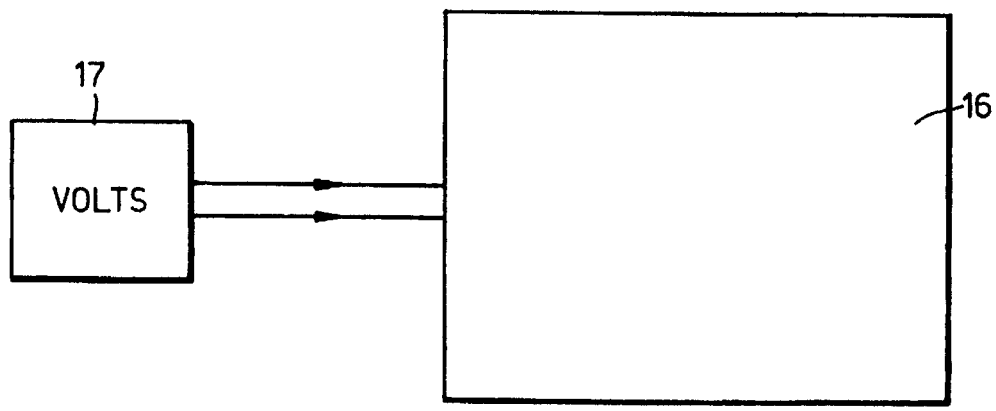
FIG. 4 is a block diagram of a reflective spatial light modulator in which the materials of the invention may be incorporated.
Figure 5:
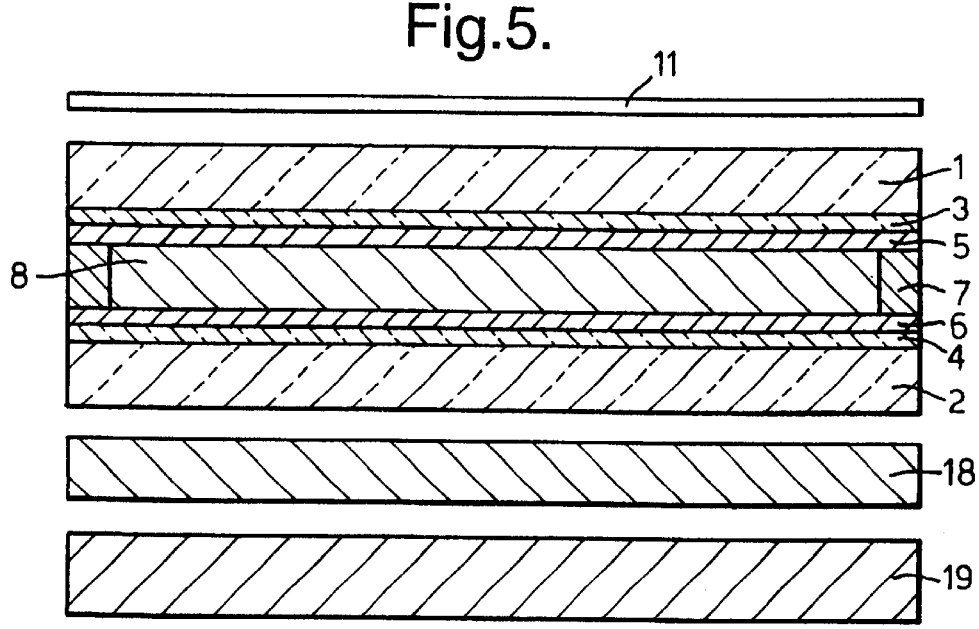
FIG. 5 is a detailed cross-sectional view of the liquid crystal cell of FIG. 4.

As shown in FIGS. 4 and 5 a spatial light modulator comprises a liquid crystal cell 16 formed by typically two glass walls 1 and 2 and 0.1–10 μm e.g. 2.5 μm thick spacer 7. The inner faces of the walls carry thin transparent indium tin oxide electrodes 3,4 connected to a variable voltage source 17. On top of the electrodes 3,4 are surface alignment layers 5,6 e.g. of rubbed polyimide. Other alignment techniques are also suitable e.g. non-rubbing techniques such as evaporation of SiO₂. A layer 8 of liquid crystal material is contained between the walls 1,2 and spacer 7. In front of the cell 16 is a linear polariser 11; behind the cell 16 is a quarter plate 18 (this may be optional) and a mirror 19. An example of a linear polariser is a polarising beam splitter (not illustrated here).

There are a variety of electroclinic devices in which the compounds of the present invention may be incorporated. For example in the above description of FIGS. 4 and 5, active back plane driving may be utilised. One of the walls forming the cell may be formed from a silicon substrate e.g. a wafer which possesses circuitry for driving pixels.

For many of these devices there exists an optimum thickness for the cell which is related to the birefringence (Δn) given by:

$$d = \frac{(2m+1)\lambda}{4(\Delta n)}$$

wherein
λ=wavelength of operation
Δn=birefringence of liquid crystalline material
m=integer.

Some suitable methods for driving electroclinic devices described by the present invention may be found in UK patent application GB-2 247 972 A.

The mode of operation of the devices described by the current invention includes either amplitude modulation or phase modulation. Similarly devices may be used in reflectance or transmissive mode.

The materials of this aspect of the invention may be used in many of the known forms of liquid crystal display devices, for example chiral smectic electro-optic devices. Such a device may comprise a layer of liquid crystal material contained between two spaced cell walls bearing electrode structures and surface treated to align liquid crystal material molecules. The liquid crystal mixtures may have many applications including in ferroelectric, thermochromic and electroclinic devices. Further examples of uses for the current materials may be found in Chem. Rev. 1995, 95, 1409–30.

The compounds of the present invention may be mixed with each other to form useful liquid crystal mixtures, they may also be used with other liquid crystal polymers or low molar mass non-polymer liquid crystal materials.

Suitable devices in which the materials of the current invention may be incorporated include beam steerers, shutters, modulators and pyroelectric and piezoelectric sensors.

The materials of the present invention may also be useful as dopants in ferroelectric liquid crystal devices, which may be multiplexed, or they may be used in active backplane ferroelectric liquid crystal systems. The materials of the present invention may also be useful as host materials. The materials of the present invention may be included in mixtures which also contain one or more dopants.

Compounds of formula I may be mixed with a wide range of hosts, for example smectic hosts to form a useful liquid crystal composition. Such compositions can have a range of Ps values. Compounds of formula I may be mixed with one or more of the types of hosts VIII—XIII. These different types of hosts may be mixed together to which the compound of general formula I may also be added.

Typical hosts include:
The compounds described in PCT/GB86/00040, e.g. of formula VIII

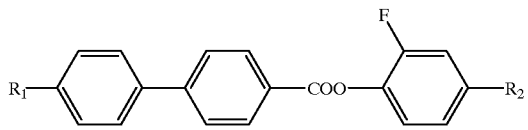

where $R_1$ and $R_2$ are independently $C_3$–$C_{12}$ alkyl or alkoxy.

The fluoro-terphenyls described in EPA 84304894.3 and GBA 8725928, e.g. of formula IX

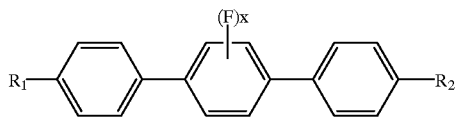

where $R_1$ and $R_2$ are independently $C_3$–$C_{12}$ alkyl or alkoxy, x is 1 and F may be on any of the available substitution positions on the phenyl ring specified.

The difluoro-terphenyls described in GBA 8905422.5, e.g. of formula X

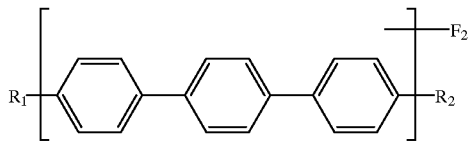

where $R_1$ and $R_2$ are independently $C_3$–$C_{12}$ alkyl or alkoxy.

The phenyl-pyrimidines described in WO 86/00087, e.g. of formula XI.

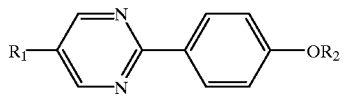

including those compounds where $R_1$ is $C_3$–$C_{12}$ alkyl and $R_2$ is given by the general formula $(CH_2)_n$—$CHXCH_2CH_3$, where n is 1 to 5 and X is CN or Cl.

The compounds described by R Eidenschink et al in Cyclohexanederivative mit Getilteneten Smektischen Phasen at the 16th Freiberg Liquid Crystal Conference, Freiberg, Germany, p8. Available from E Merck Ltd, Germany, e.g. of formula XII.

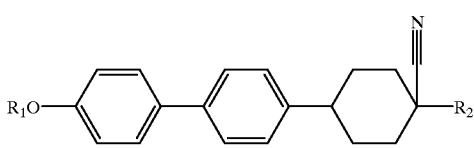

XII including those compounds where $R_1$ and $R_2$ are independently $C_1$–$C_{15}$ alkyl.

The difluoro-phenyl pyrimidines described at the 2$^{nd}$ International Symposium on Ferroelectric Liquid Crystals, Göteborg, Sweden, June 1989 by Reiffenrath et al, e.g. of formula XIII

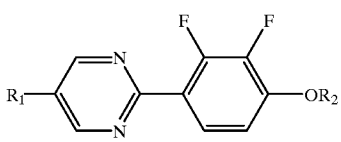

XIII including those compounds where $R_1$ and $R_2$ are independently $C_3$–$C_9$ alkyl.

The materials of the current invention may also be useful in thermochromic devices, for example those devices described by D. G, McDonnell in Thermochromic Liquid Crystals, Critical Reports on Applied Chemistry, vol. 22, edited by G. W. Gray, 1987 pp120–44 and references therein.

What is claimed is:

1. A material of general formula I

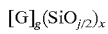     I wherein G is $R_3SiR_1R_2(O)_k$;

$R_1$, $R_2$, $R_3$ are independently selected from $C_{1-16}$ alkyl which may be partly or fully halogenated, H and formula IA:

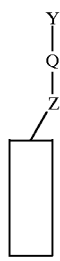

IA wherein Y is selected from COO, OCO, O, S, CHOH, CHF and $CH_2$;

Q=$(CH_2)_n$ wherein one or more non-adjacent methylenes may be replaced by O and n=1–20;

Z is selected from O, S, single covalent bond, COO, OCO;

when Y is $CH_2$ then n may also be 0;

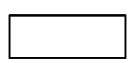

represents a mesogenic group of the following general formula II:

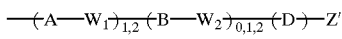

where A, B and D are independently selected from the following rings:

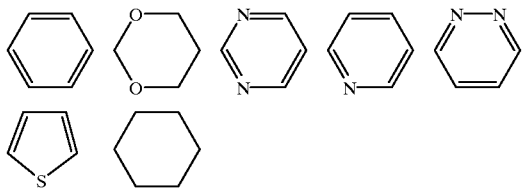

and the above rings may be substituted with one or more of the following substituents in at least one of the available substitution positions: F, Cl, Br, $CH_3$, CN, OR, R and NCS where R is a $C_{1-5}$ a straight chain alkyl or a branched $C_{3-5}$ alkyl;

Z' is selected from CN, F, Cl, $NO_2$, R, OR, COOR, $CF_3$, OOCR, NCS, SCN, where R=a straight chain or branched chain alkyl having from 1–16 carbon atoms and including where one or more non-adjacent $CH_2$ groups may be substituted by CH(CN), CH($CF_3$), CH(Cl) or CH($CH_3$) in chiral or non-chiral form;

provided that the total number of rings present in formula II is not greater than 4; and $W_1$ and $W_2$ are independently selected from COO, OCO, single bond, $CH_2CH_2$, $CH_2O$, $OCH_2$, O, S, CH=CH and C≡C;

provided that:

Z' is selected from CN, OR and COOR; or the core is selected from:

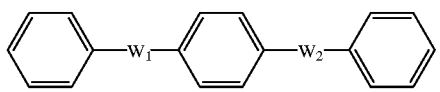

wherein $W_1$ and $W_2$ are selected from COO, OCO and a single bond, provided that one of $W_1$ and $W_2$ is selected from COO or OCO;

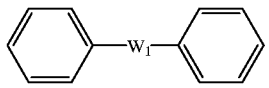

wherein $W_1$ is selected from COO, OCO and a single bond; provided that at least one of $R_1$, $R_2$, $R_3$ is selected from formula IA;

k is 1 then x is selected from 6, 8, 10, 12; j=3 and g=x;

when k is 0 then x is 1, j=8 and g=4 or further provided that G may have up to g different structures for any single compound;

and further provided that when Y and Q together only comprises an alkylene group then there are at least four carbon atoms present;

and provided that when k=0, j=8, g=4 and x=1 then Z' is selected from OR or COOR or OOCR where R is $C_{3-16}$ branched chain alkyl.

2. A material according to claim 1 wherein $R_1$, $R_2$ and $R_3$ are all chosen from formula IA.

3. A material according to claim 2 wherein x is 6 or 8.

4. A liquid crystal mixture comprising at least one of the compounds of claim 1.

5. A ferroelectric mixture comprising at least one of the compounds of claim 1.

6. A cholesteric liquid crystal mixture comprising at least one of the compounds of claim 1.

7. A liquid crystal mixture containing any of the compounds of claim 1 and a material of the following general formula:

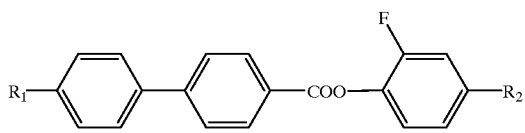

where $R_1$ and $R_2$ are independently $C_3$–$C_{12}$ alkyl or alkoxy.

8. A liquid crystal mixture containing any of the compounds of claim 1 and a material of the following general formula:

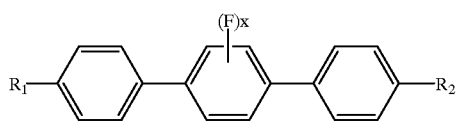

where $R_1$ and $R_2$ are independently $C_3$–$C_{12}$ alkyl or alkoxy, x is 1 and F may be on any of the available substitution positions on the phenyl ring specified.

9. A liquid crystal mixture containing any of the compounds of claim 1 and a material of the following general formula:

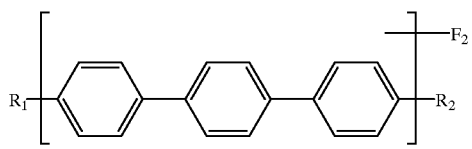

where $R_1$ and $R_2$ are independently $C_3$–$C_{12}$ alkoxy.

10. A liquid crystal mixture containing any of the compounds of claim 1 and a material of the following general formula:

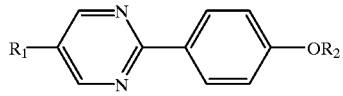

including those compounds where $R_1$ is $C_3$–$C_{12}$ alkyl and $R_2$ is given by the general formula $(CH_2)_n$—$CHXCH_2CH_3$, where n is 1 to 5 and X is CN or Cl.

11. A liquid crystal mixture containing any of the compounds of claim 1 and a material of the following general formula:

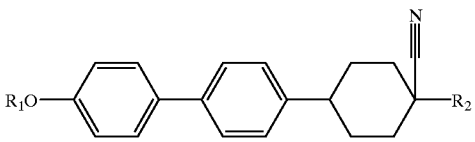

including those compounds where $R_1$ and $R_2$ are independently $C_1$–$C_{15}$ alkyl.

12. A liquid crystal mixture containing any of the compounds of claim 1 and a material of the following general formula:

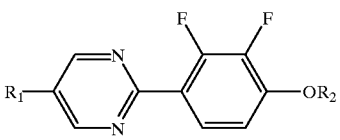

including those compounds where $R_1$, and $R_2$ are independently $C_3$–$C_9$ alkyl.

13. A device comprising two spaced cell walls each bearing electrode structures and treated on at least one facing surface with an alignment layer, a layer of a liquid crystal material enclosed between the cell walls, characterised in that it incorporates the liquid crystal mixture as claimed in claim 4.

14. A pyroelectric device comprising two spaced electrodes and a layer of a liquid crystal material enclosed between the electrodes, characterised in that it incorporates the liquid crystal mixture as claimed in claim 4.

15. A piezoelectric device comprising two spaced electrodes and a layer of a liquid crystal material enclosed between the electrodes, characterised in that it incorporates the liquid crystal mixture as claimed in claim 4.

16. A liquid crystal electro-optical display device characterised in that it incorporates a mixture as claimed in claim 4.

17. An optical recording medium comprising a recording layer which comprises one or more compounds of claim 1 and a dye material.

* * * * *